(12) United States Patent
Li et al.

(10) Patent No.: US 9,078,475 B2
(45) Date of Patent: Jul. 14, 2015

(54) ATOMIZING DEVICE AND ELECTRONIC CIGARETTE HAVING SAME

(71) Applicant: Shenzhen First Union Technology Co., Ltd., Shenzhen (CN)

(72) Inventors: Yonghai Li, Shenzhen (CN); Zhongli Xu, Shenzhen (CN); Xianming Wang, Shenzhen (CN); Wen Luo, Shenzhen (CN); Yunping Zhong, Shenzhen (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 0 days.

(21) Appl. No.: 14/189,831

(22) Filed: Feb. 25, 2014

(65) Prior Publication Data

US 2014/0332021 A1 Nov. 13, 2014

(30) Foreign Application Priority Data

May 7, 2013 (CN) .......................... 2013 1 0167404

(51) Int. Cl.
*A24F 47/00* (2006.01)
*A61M 15/06* (2006.01)
*H05B 3/03* (2006.01)

(52) U.S. Cl.
CPC ............. *A24F 47/008* (2013.01); *A24F 47/002* (2013.01); *A61M 15/06* (2013.01); *H05B 3/03* (2013.01)

(58) Field of Classification Search
CPC ..... A24F 47/002; A24F 47/008; A61M 15/06
USPC .............................. 131/273, 329; 128/202.21
See application file for complete search history.

(56) References Cited

U.S. PATENT DOCUMENTS

| 2009/0095311 | A1* | 4/2009 | Han | 131/194 |
| 2010/0229881 | A1* | 9/2010 | Hearn | 131/273 |
| 2011/0120455 | A1* | 5/2011 | Murphy | 128/200.18 |
| 2014/0334803 | A1* | 11/2014 | Li et al. | 392/394 |
| 2014/0355969 | A1* | 12/2014 | Stern | 392/390 |

* cited by examiner

*Primary Examiner* — Anthony Calandra
(74) *Attorney, Agent, or Firm* — Winstead PC (57) ABSTRACT

An atomizing device includes an atomizing sleeve; a mouthpiece assembly and an atomizing assembly received in the atomizing sleeve. The atomizing assembly includes an oil obstructing ring, a supporting sleeve, a porous body being fixed between the oil obstructing ring and the supporting sleeve, a heating wire wrapping around the porous body, a screw sleeve located at an end of the atomizing sleeve, an insulated ring and an tubular electrode received between the screw sleeve and the insulated ring. An oil valve is formed between the supporting sleeve and the tubular electrode, or between the tubular electrode and the insulated ring; the oil valve is opened or closed by a movement of the tubular electrode, and the oil valve is configured as an air passage in communication with the air pipe when the oil valve is opened. An electronic cigarette using the atomizing device is also provided.

11 Claims, 11 Drawing Sheets

ATOMIZING DEVICE AND ELECTRONIC CIGARETTE HAVING SAME

BACKGROUND

1. Technical Field

The present invention relates to atomizing devices, and particularly to an atomizing device and an electronic cigarette having the atomizing device.

2. Description of Related Art

Electronic cigarettes are similar to conventional cigarettes in appearance and taste, but less harmful to human's health, so that electronic cigarettes are widely used for helping people to quit smoke. Atomizing devices are key components of electronic cigarettes. A typical atomizing device includes a tobacco oil reserving space and an atomizing assembly. The atomizing assembly has a porous body extending into the tobacco oil reserving space to get the tobacco oil, and the tobacco oil is also sealed by the porous body. However, this configuration may cause the tobacco oil leak out of the atomizing device.

What is needed, therefore, is an atomizing device and an electronic cigarette which can overcome the above shortcomings.

BRIEF DESCRIPTION OF THE DRAWINGS

Many aspects of the present atomizing device and electronic cigarette can be better understood with reference to the following drawings. The components in the drawings are not necessarily drawn to scale, the emphasis instead being placed upon clearly illustrating the principles of the present atomizing device and electronic cigarette. Moreover, in the drawings, like reference numerals designate corresponding parts throughout the several views.

DETAILED DESCRIPTION

Embodiments of the present electronic cigarette will now be described in detail below and with references to the drawings.

Figure 1:
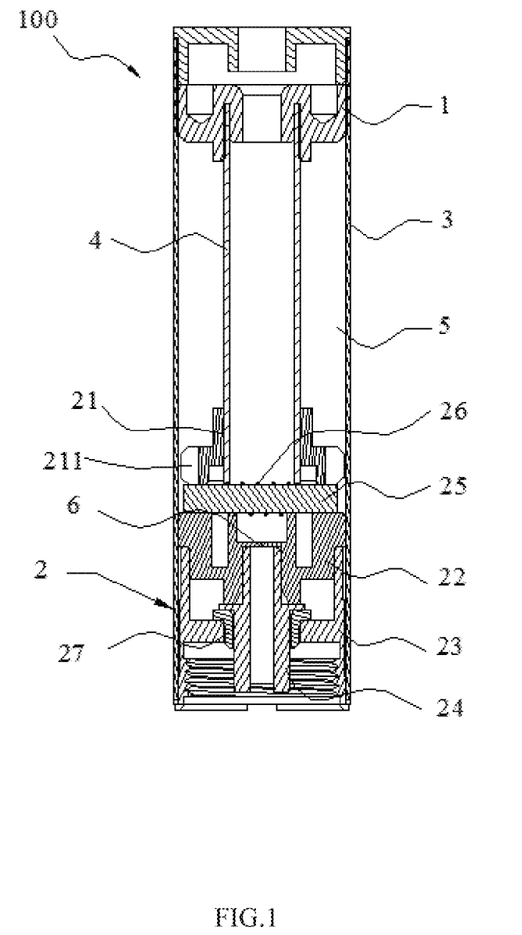
FIG. 1 is a schematic cross sectional view of an atomizing device of an electronic cigarette in accordance with a first embodiment.
Figure 2:
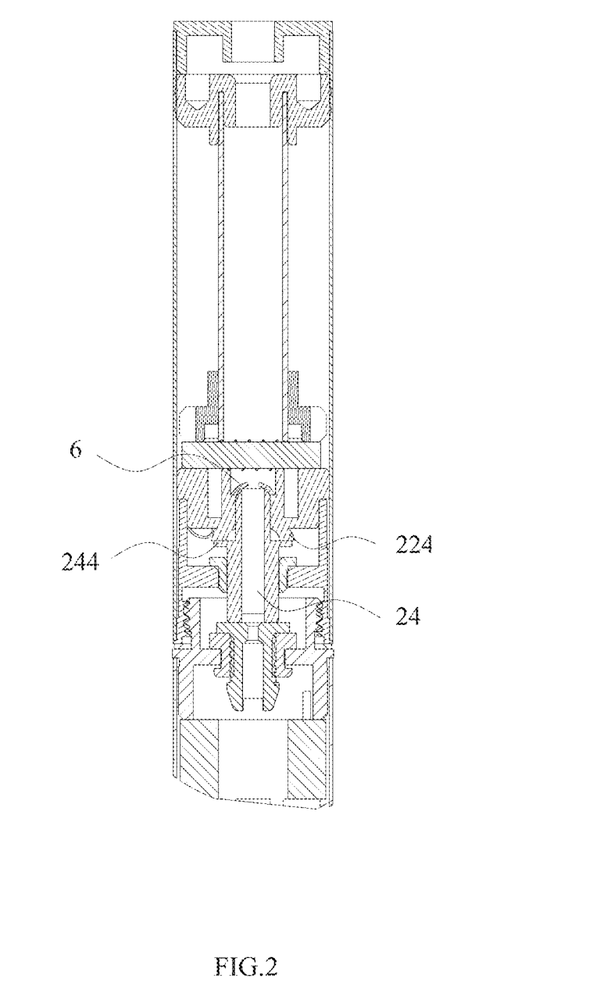
FIG. 2 shows an application state of the electronic cigarette of FIG. 1.

Referring to FIGS. 1 and 2, an atomizing device 100 of an electronic cigarette in accordance with a first embodiment is provided. The atomizing device 100 mainly includes a mouthpiece assembly 1, an atomizing assembly 2, and an atomizing sleeve 3. The mouthpiece assembly 1 and the atomizing assembly 2 are received in the atomizing sleeve 3, and are respectively positioned at two ends of the atomizing sleeve 3. The mouthpiece assembly 1 and the atomizing assembly 2 are connected through an air pipe 4 received in the atomizing sleeve 3. A liquid reserving space 5 defined between the atomizing sleeve 3 and the air pipe 4 is for reserving a tobacco oil.

The atomizing assembly 2 includes an oil obstructing ring 21, a supporting sleeve 22, a screw sleeve 23, a tubular electrode 24, a porous body 25, and a heating coil 26 wrapping around the porous body 25. The porous body 25 is arranged on the supporting sleeve 22, and the oil obstructing ring 21 is arranged on the porous body 25. The oil obstructing ring 21 has an oil hole 211 for the tobacco oil getting through to reach the porous body 25. A diameter of the oil hole 211 can be predetermined to limit a flow rate of the tobacco oil. One end of the heating coil 26 is electrically connected to the tubular electrode 24, and the other end of the heating coil 26 is electrically connected to screw sleeve 23.

Figure 3:
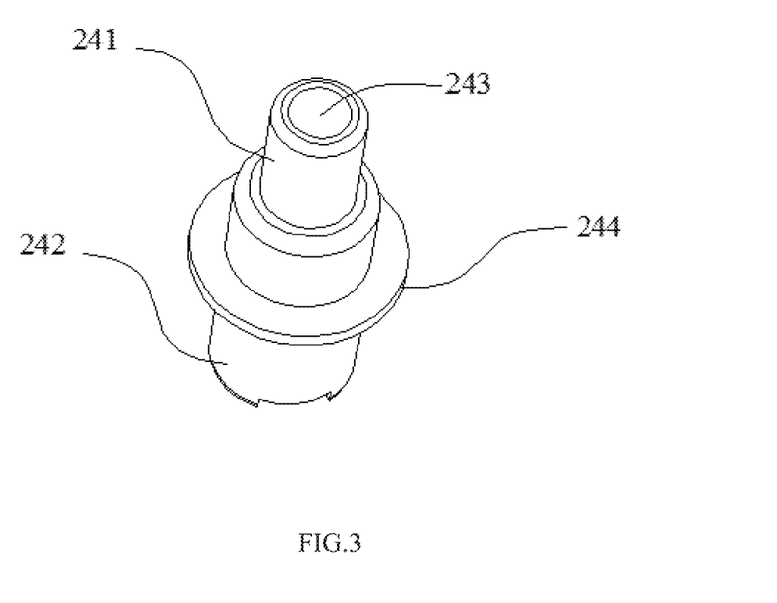
FIG. 3 is an isometric view of a tubular electrode used in FIG. 1.

Referring also to FIG. 3, the tubular electrode 24 includes an inner hole 243, a front end 241 and a rear end 242. The front end 241 is movably received in the supporting sleeve 22, and the rear end 242 is movably received in the screw sleeve 23. An insulating ring 27 is arranged between the rear end 242 and the screw sleeve 23, and an oil valve 6 is located between the front end 241 and the supporting sleeve 22. The tubular electrode 24 is movable in the supporting sleeve 22 and the insulating ring 27 along axes of the supporting sleeve 22 and the insulating ring 27, thereby the oil valve 6 is opened or closed as the tubular electrode 24 moves upwards or downwards, and an air passage of the atomizing device 100 is thus opened up or closed.

Figure 4:
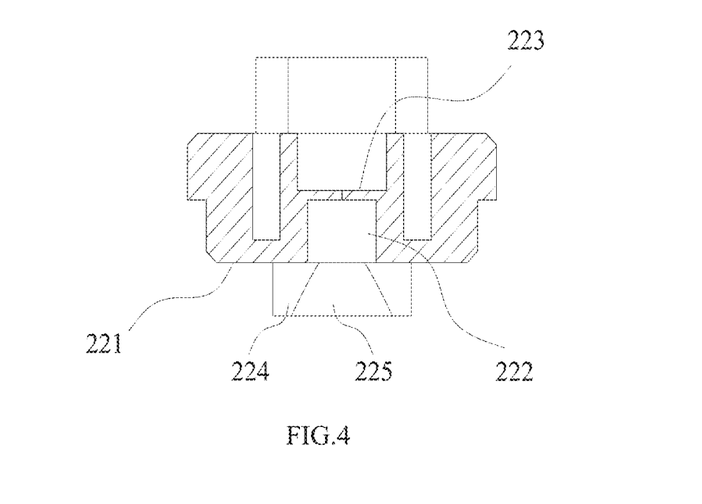
FIG. 4 is a schematic cross sectional view of a supporting sleeve used in FIG. 1.

Specially, referring also to FIG. 4, the supporting sleeve 22 includes a fitting hole 222 for receiving the front end 241 of the tubular electrode 24. The oil valve 6 is located inside the fitting hole 222. In the present embodiment, the oil valve 6 includes two sheets 223 which are integrally formed with the supporting sleeve 22. The fitting hole 222 is sealed when the sheets 223 are folded, and the fitting hole 222 is got through when the sheets 223 are unfolded. As the tubular electrode 24 moves upwards, the sheets 223 are unfolded by the front end 241 of the tubular electrode 24, the fitting hole 222 is got through, and the air passage of the atomizing device 100 is thus opened up. As the tubular electrode 24 moves downwards, the sheets 223 are folded again, the fitting hole 222 is sealed, and the oil valve 6 can prevent the oil from leaking out of the atomizing device 100.

Referring again to FIGS. 3 and 4, the supporting sleeve 22 includes a projection 224 projecting from a bottom surface 221 of the supporting sleeve 22. In the present embodiment, the supporting sleeve 22 is made of a silicon rubber capable of withstanding a high temperature of the atomizing device 100, and the projection 224 has a resilience due to the silicon rubber. The projection 224 has a through hole 225 in communication with the fitting hole 222. The tubular electrode 24 includes a flange 244 formed between the front end 241 and the back end 242, and a diameter of the flange 244 is greater than that of the projection 224. As the front end 241 of the tubular electrode 24 is moved in the fitting hole 222 of the supporting sleeve 22, the flange 244 first contacts the projection 224, then compresses the projection 224 until the sheets 223 are unfolded by the front end 241 of the tubular electrode 24. The tubular electrode 24 may return to an original position due to the resilience of the projection 224. In the present embodiment, the through hole 225 is tapering shaped to make the projection 224 has a better resilience.

Figure 5:
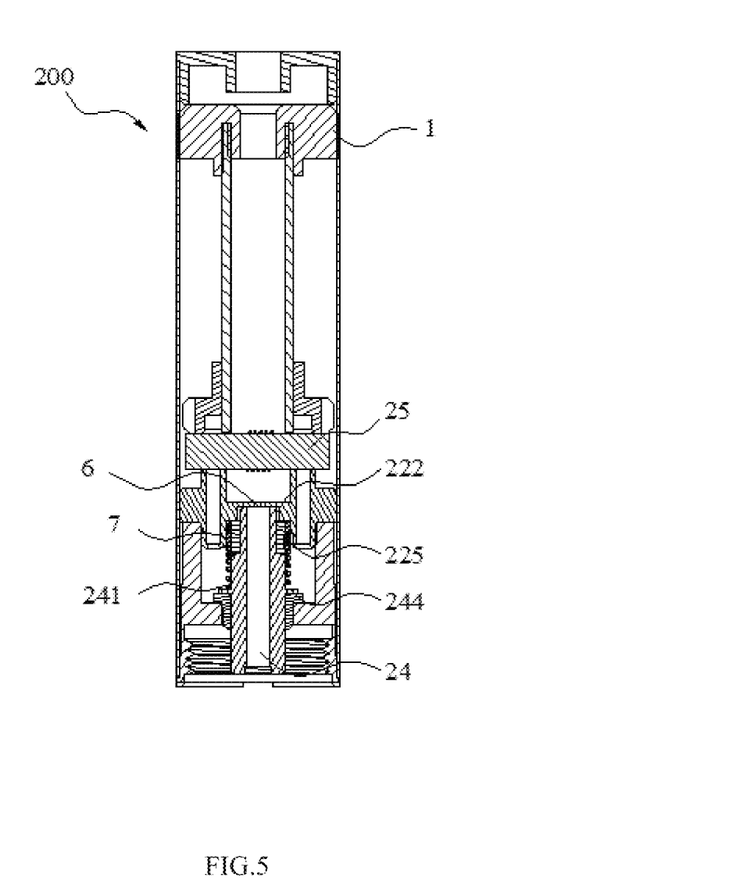
FIG. 5 is a schematic cross sectional view of an atomizing device of an electronic cigarette in accordance with a second embodiment.

Referring to FIG. 5, an atomizing device 200 of an electronic cigarette in accordance with a second embodiment is provided. The atomizing device 200 is similar to the atomizing device 100 illustrated above, the difference that the atomizing device 200 different from the atomizing device 100 is: both of the through hole 225 and the fitting hole 222 are cylindrical shaped, and a diameter of the through hole 225 is greater than that of the fitting hole 222, so that the fitting hole 222 and the through hole 225 form a stepped hole. An elastic member 7 is fixed on the front end 241 between the through hole 225 and the flange 244. The elastic member 7 can be compressed by a movement of the tubular electrode 24 toward the oil valve 6, and can help the tubular electrode 24 return to an original position due to a resilience of the elastic member 7.

Figure 6:
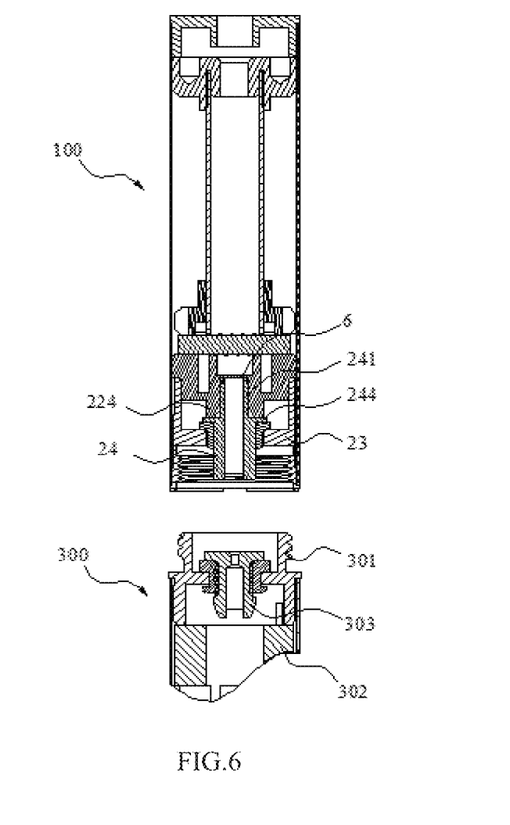
FIG. 6 is a schematic cross sectional view of an electronic cigarette in accordance with a third embodiment.

Referring to FIG. 6, an electronic cigarette in accordance with a third embodiment is provided. The electronic cigarette includes an atomizing device 100 and a battery assembly 300. The battery assembly 300 includes a battery 302, a screw sleeve 301, and an electrode ring 303 fixed in the screw sleeve 301. The screw sleeve 301 is threadedly connected to the screw sleeve 23 and the electrode ring 303 contacts and pushes the tubular electrode 24 to move toward the oil valve 6 to open up the oil valve 6 when the battery assembly 300 is connected to the atomizing device 100, thereby, the air passage is got through and the atomized tobacco oil can be sucked out by user. The tubular electrode 24 can return to an original position due to the resilient projection 224 or the elastic member 7 to close the oil valve 6 when the battery assembly 300 is disconnected from the atomizing device 100, thereby, the tobacco oil in the atomizing device 100 would not leak out.

Referring to FIGS. 7 to 10, an atomizing device 400 of an electronic cigarette in accordance with a fourth embodiment is provided. In the atomizing device 400, an inner diameter of the fitting hole 222 is equal to an outer diameter of the front end 241 of the tubular electrode 24, and the tubular electrode 24 has an inner hole 243, and two air inlets 246 and two air outlets 245 in communication with the inner hole 243. The front end 241 has a cover 248 integrally formed therewith. The air inlets 246 and the air outlets 245 are formed at a peripheral wall of the inner hole 243, and the air outlets 245 are adjacent to the cover 248 of the front end 241. The inner hole 243 goes through the back end 242.

Figure 7:
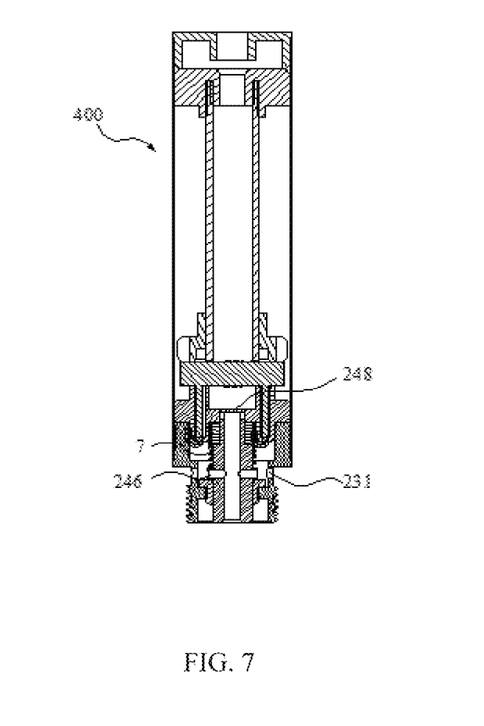
FIG. 7 is a schematic cross sectional view of an atomizing device of an electronic cigarette in accordance with a fourth embodiment.
Figure 8:
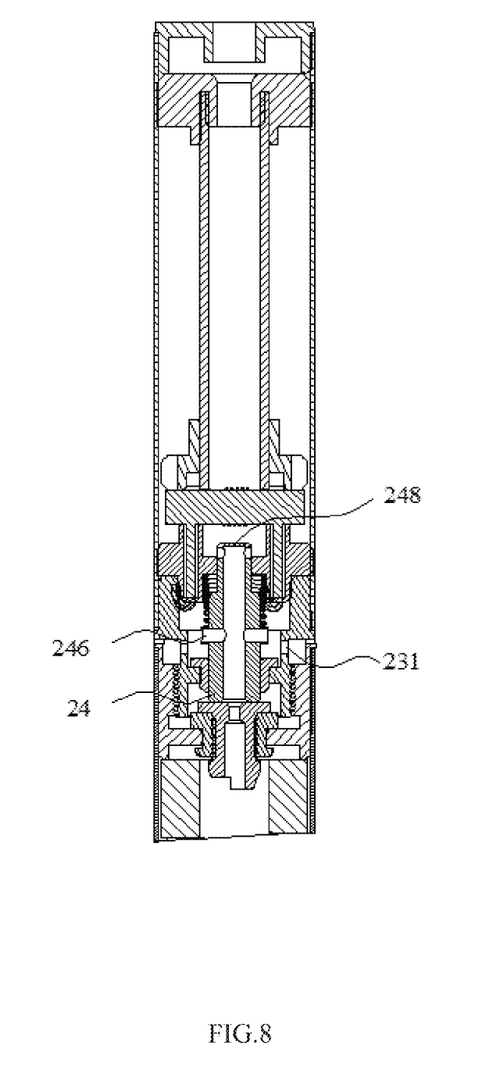
FIG. 8 shows an application state of the electronic cigarette of FIG. 7.

The air outlets 245 are sealed in the fitting hole 222 by the cover 248 of the front end 241 while the front end 241 lies in the fitting hole 222, thus, a closed air valve is formed, and the tobacco oil would not leak out of the atomizing device 400 (see FIG. 7). The air outlets 245 are exposed out of the air pipe 4 as the tubular electrode 24 is moved upwards, thereby the oil valve is opened, and configured as an air passage, and the atomized tobacco oil can be sucked out by the user (see FIG. 8).

Figure 9:
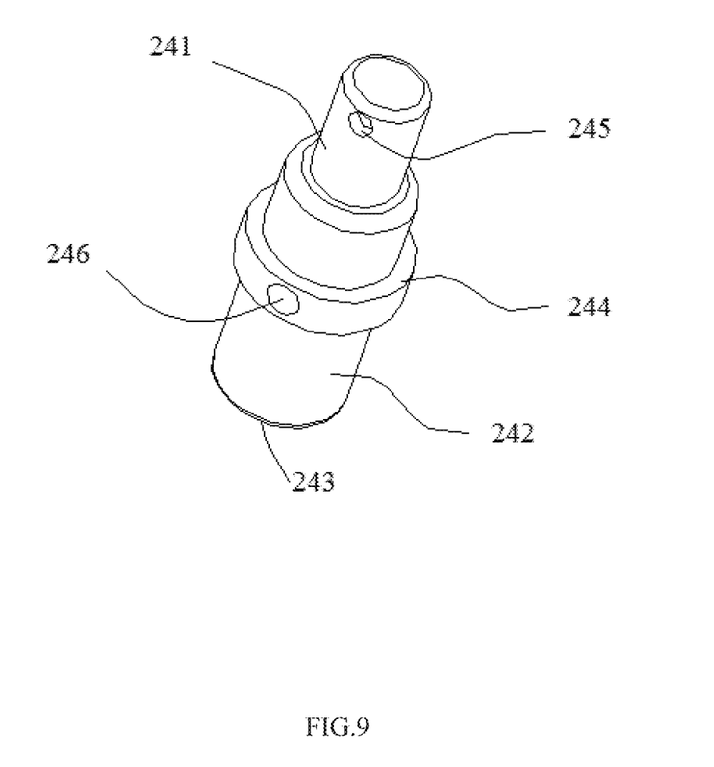
FIG. 9 is an isometric view of a tubular electrode used in FIG. 7.
Figure 10:
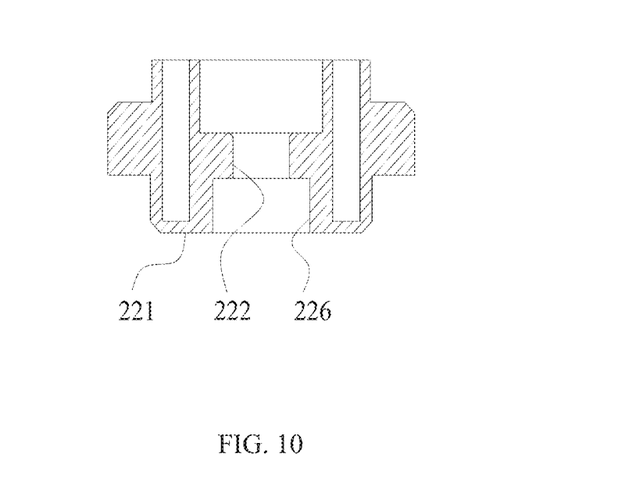
FIG. 10 is a schematic cross sectional view of a supporting sleeve used in FIG. 7.

Referring to FIGS. 9 and 10, the supporting sleeve 22 also has a through hole 226 formed therein and in communication with the fitting hole 222. A diameter of the through hole 226 is greater than that of the fitting hole 222. The tubular electrode 24 also has a flange 244 and an elastic member 7 being positioned between the through hole 226 and the flange 244. The resilience of the elastic member 7 can help the front end 241 of the tubular electrode 24 return to the fitting hole 222 after being moved out of the fitting hole 222.

In addition, the screw sleeve 23 has an orifice 231 in communication with the inner space of the atomizing device 400. Air enters into the atomizing device 300 through the orifice 231.

Referring to FIGS. 11 to 14, an atomizing device 500 of an electronic cigarette in accordance with a fifth embodiment is provided. In the atomizing device 500, the insulated ring 27 includes a stepped hole 271 with a flexible inner flange 2713. The stepped hole 271 further includes a lower section 2711 and an upper section 2712, the flange 2713 is located between the lower section 2711 and the upper section 2712, and a diameter of the lower section 2711 is less than that of the upper section 2712. The tubular electrode 24 includes a front sleeve 240 and a back block 249. The front sleeve 240 is engaged in the supporting sleeve 22. The front sleeve 240 has a central through hole 2401 and a cutout 247 formed in a wall of the central through hole 2401 and in communication with the central through hole 2401. An outer diameter of the flange 244 of the back block 249 is substantially equal to an inner diameter of the lower section 2711. The back block 249 has an inner hole 243 and a ring-shaped slot 248 formed in a peripheral wall of the inner hole 243 and in communication with the inner hole 243. The back block 249 has a front end 2491 received in the central through hole 2401.

Figure 11:
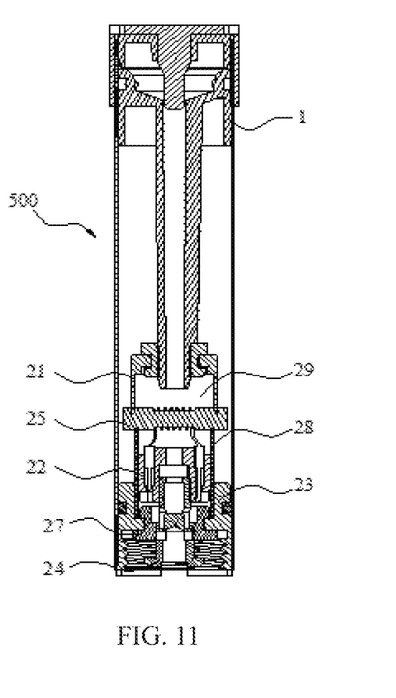
FIG. 11 is a schematic cross sectional view of an atomizing device of an electronic cigarette in accordance with a fifth embodiment.
Figure 12:
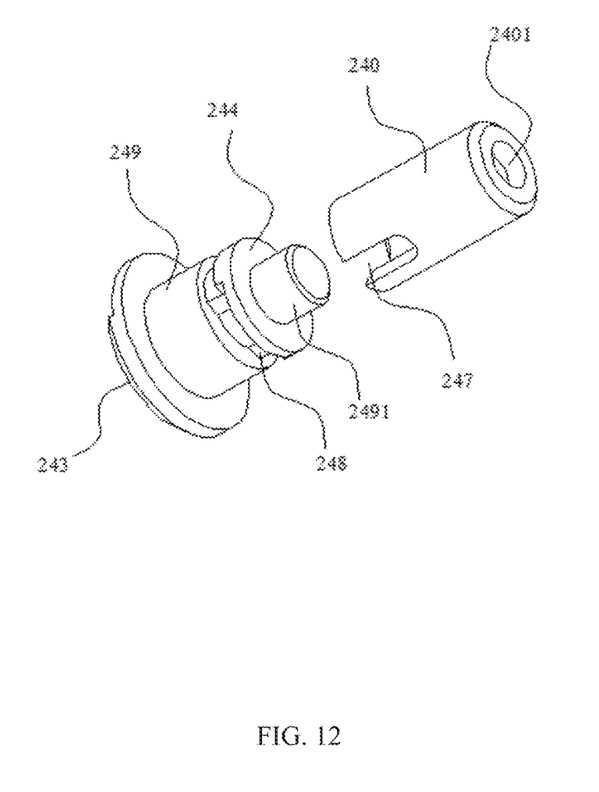
FIG. 12 is an isometric view of a tubular electrode used in FIG. 11.
Figure 13:
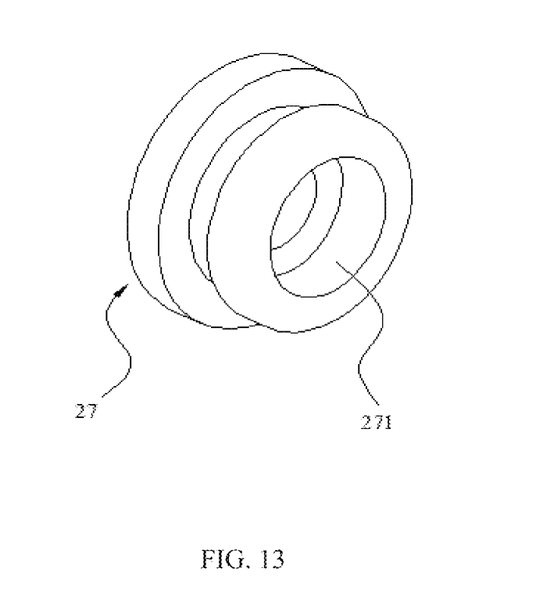
FIG. 13 is an isometric view of an insulated ring used in FIG. 11.
Figure 14:
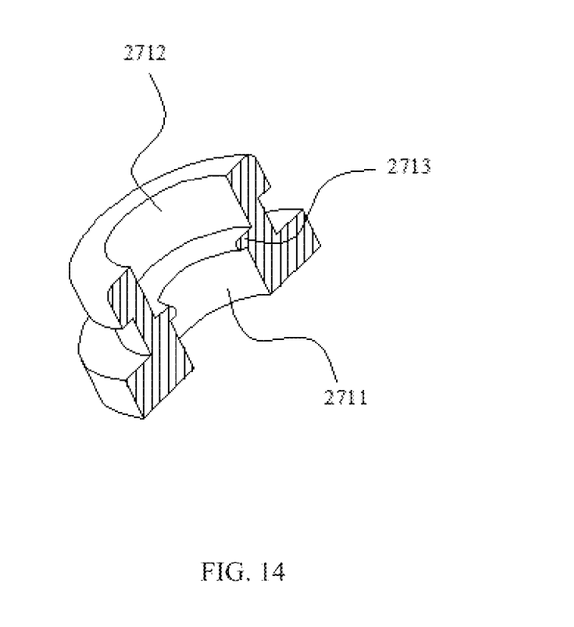
FIG. 14 is a cross sectional view of the insulated ring of FIG. 13.

In a situation that the atomizing device 500 does not work, the flange 244 of the tubular electrode 24 stays at the lower section 2711 and abuts on the inner flange 2713 of the insulated ring 27, thereby forming a closed oil valve, then the tobacco oil in the atomizing device 500 would not leak out. In another situation, the tubular electrode 24 is push towards the atomizing device 500 by the battery assembly when a battery assembly is connected to the atomizing device 500, then the flange 244 leaps to the upper section 2712 of the insulated ring 27, and the inner flange 2713 would leaps into the ring-shaped slot 248. In this situation, the air valve is opened, and configured as an air passage for air passing through the inner hole 243, the ring-shaped slot 248, the upper section 2712, the cutout 247, the central through hole 2401, the supporting sleeve 22, and the air pipe 4, then the atomizing device 500 begins to work.

Referring again to FIG. 11, in the present embodiment, a sealing sleeve 28 is provided between the oil obstructing ring 21 and the supporting sleeve 22. The oil obstructing ring 21, the supporting sleeve 22, and the sealing sleeve 28 cooperatively form an atomizing chamber 29 in communication with the air pipe 4 and the supporting sleeve 22. The porous body 25 is positioned between the oil obstructing ring 21 and the sealing sleeve 28 and the heating coil is received in the atomizing chamber 29. The tobacco oil is atomized in the atomizing chamber 29 to form aerosol, and the aerosol can be sucked out by the mouthpiece assembly through the air passage.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizing device of an electronic cigarette, comprising:

an atomizing sleeve;

a mouthpiece assembly and an atomizing assembly received in the atomizing sleeve, the mouthpiece assembly and the atomizing assembly being connected through an air pipe, and a liquid reserving space being formed between the atomizing sleeve and the air pipe;

wherein the atomizing assembly comprises an oil obstructing ring located at an end of the air pipe, a supporting sleeve, a porous body being fixed between the oil obstructing ring and the supporting sleeve, a heating wire wrapping around the porous body, a screw sleeve located at an end of the atomizing sleeve, an insulated ring, and an tubular electrode received between the screw sleeve and the insulated ring, two ends of the heating wire are respectively electrically connected to the tubular electrode and the screw sleeve, wherein an oil valve is formed between the supporting sleeve and the tubular electrode, or between the tubular electrode and the insulated ring; the oil valve is opened or closed by a movement of the tubular electrode, and the oil valve is configured as an air passage in communication with the air pipe when the oil valve is opened.

2. The atomizing device of claim 1, wherein the oil valve is two sheets integrally formed with an inner wall of the supporting sleeve.

3. The atomizing device of claim 2, wherein the supporting sleeve includes a fitting hole, the oil valve is located inside the fitting hole, and the tubular electrode includes a front portion received in the fitting hole and an inner hole forming at least one part of the air passage.

4. The atomizing device of claim 3, wherein the tubular electrode further includes a flange, and an elastic member is positioned between the flange and the fitting hole.

5. The atomizing device of claim 1, wherein the tubular electrode includes an inner hole, an air outlet formed in a wall of the inner hole and in communication with the inner hole, and a cover covering the inner hole and the air outlet, the air outlet in contact with an inner wall of the supporting sleeve, thereby forming the oil value.

6. The atomizing device of claim 5, wherein the tubular electrode further comprises an air inlet, and the screw sleeve includes an orifice opposite to the air inlet.

7. The atomizing device of claim 1, wherein the insulated ring comprises a stepped hole including an upper section and a lower section, a flexible inner flange located between the upper section and the lower section, the tubular electrode comprises a front portion engaged in the supporting sleeve and a back portion, the front portion has a central through hole and a cutout in communication with the central through hole, the back portion includes a flange abutting on the inner flange of the insulated ring, a central hole and a ring-shaped slot in communication with the central hole, the slot in contact with an inner wall of the lower section of the stepped hole to form the oil valve.

8. The atomizing device of claim 7, wherein the central hole, the slot, the upper section of the stepped hole, the cutout, and the central through hole cooperatively form at least one part of the air passage.

9. The atomizing device of claim 1, further comprising a sealing sleeve formed between the oil obstructing ring and the supporting sleeve, the porous body is positioned on the sealing sleeve.

10. The atomizing device of claim 9, wherein the oil obstructing ring and the sealing sleeve cooperatively form an atomizing chamber.

11. An electronic cigarette comprising an atomizing device of claim 1, and a battery assembly connected to the atomizing device, the battery assembly comprises an electrode ring to push the tubular electrode of the atomizing device to move.

\* \* \* \* \*